United States Patent
Iyer et al.

(10) Patent No.: US 8,835,706 B2
(45) Date of Patent: Sep. 16, 2014

(54) PROCESS FOR THE CONVERSION OF MIXED LOWER ALKANES TO AROMATIC HYDROCARBONS

(75) Inventors: Mahesh Venkataraman Iyer, Houston, TX (US); Ann Marie Lauritzen, Houston, TX (US); Ajay Madhav Madgavkar, Katy, TX (US)

(73) Assignee: Shell Oil Company, Houston, TX (US)

( * ) Notice: Subject to any disclaimer, the term of this patent is extended or adjusted under 35 U.S.C. 154(b) by 191 days.

(21) Appl. No.: 13/505,043

(22) PCT Filed: Oct. 29, 2010

(86) PCT No.: PCT/US2010/054600
§ 371 (c)(1),
(2), (4) Date: May 29, 2012

(87) PCT Pub. No.: WO2011/053747
PCT Pub. Date: May 5, 2011

(65) Prior Publication Data
US 2012/0240467 A1  Sep. 27, 2012

Related U.S. Application Data

(60) Provisional application No. 61/257,085, filed on Nov. 2, 2009.

(51) Int. Cl.
*C07C 2/42* (2006.01)
*C07C 2/46* (2006.01)
*C07C 2/76* (2006.01)

(52) U.S. Cl.
CPC .............. *C07C 2/76* (2013.01); *C07C 2521/04* (2013.01); *C07C 2529/40* (2013.01); *C07C 2529/44* (2013.01)
USPC .............................. 585/412; 585/322; 585/301

(58) Field of Classification Search
CPC .............. C07C 2/76; C07C 2/46; C07C 2/42; C07C 15/00; C07C 2521/04
USPC .......................................... 585/412, 322, 301
See application file for complete search history.

(56) References Cited

U.S. PATENT DOCUMENTS 2,854,402 A  9/1958  Rex
3,751,503 A  8/1973  Sampson et al.
(Continued)

FOREIGN PATENT DOCUMENTS

CA  2620480  4/2007
CN  86101994  9/1986
(Continued)

OTHER PUBLICATIONS

Choudhary, V. R. et al., "Effedtive Low-Temperature Aromatization of Ethane Over H-Galloaluminosilicate(MFI) Zeolites in the Presence of Higher Alkanes or Olefins", Angew Chem. Intl. Ed. Engl (1997) vol. 36, No. 12, pp. 1305-1308.
(Continued)

*Primary Examiner* — Thuan D Dang (57) ABSTRACT

A process for the conversion of mixed lower alkanes into aromatics which comprises first reacting a mixed lower alkane feed comprising at least propane and ethane in the presence of an aromatization catalyst under reaction conditions which maximize the conversion of propane into first stage aromatic reaction products, separating ethane from the first stage aromatic reaction products, reacting ethane in the presence of an aromatization catalyst under reaction conditions which maximize the conversion of ethane into second stage aromatic reaction products, and optionally separating ethane from the second stage aromatic reaction products.

15 Claims, 2 Drawing Sheets

(56) References Cited

U.S. PATENT DOCUMENTS

| | | | |
|---|---|---|---|
| 3,827,867 A | 8/1974 | Heinemann et al. | |
| 3,827,968 A | 8/1974 | Givens et al. | |
| 4,058,452 A | 11/1977 | Loboda | |
| 4,100,218 A | 7/1978 | Chen et al. | |
| 4,120,910 A | 10/1978 | Chu | 260/673 |
| 4,158,026 A | 6/1979 | Addison | |
| 4,179,474 A | 12/1979 | Beuther et al. | |
| 4,215,231 A | 7/1980 | Raymond | |
| 4,229,602 A | 10/1980 | Brinkmeyer et al. | |
| 4,288,645 A | 9/1981 | Wagstaff | |
| 4,350,835 A | 9/1982 | Chester et al. | 585/415 |
| 4,528,412 A | 7/1985 | Steacy | |
| 4,547,205 A | 10/1985 | Steacy | |
| 4,554,393 A | 11/1985 | Liberts et al. | |
| 4,613,716 A | 9/1986 | McNiff | 585/415 |
| 4,642,402 A | 2/1987 | Jensen | |
| 4,642,403 A | 2/1987 | Hyde et al. | |
| 4,665,251 A | 5/1987 | Chu | |
| 4,677,235 A | 6/1987 | Mowry | |
| 4,766,265 A | 8/1988 | Desmond et al. | |
| 4,795,845 A | 1/1989 | Martindale et al. | 585/415 |
| 4,806,699 A | 2/1989 | Smith et al. | |
| 4,806,700 A | 2/1989 | Martindale | |
| 4,808,295 A | 2/1989 | Nemet-Mavrodin | 208/65 |
| 4,849,568 A | 7/1989 | McCullen et al. | |
| 4,855,522 A | 8/1989 | Diaz | |
| 4,857,498 A | 8/1989 | Dejaifve et al. | 502/304 |
| 4,861,932 A | 8/1989 | Chen et al. | |
| 4,899,006 A | 2/1990 | Dave et al. | 585/415 |
| 4,912,273 A | 3/1990 | Harandi et al. | |
| 4,968,401 A | 11/1990 | Harandi et al. | |
| 4,996,381 A | 2/1991 | Pickering, Jr. et al. | |
| 5,013,423 A | 5/1991 | Chen et al. | |
| 5,019,663 A | 5/1991 | Chou et al. | |
| 5,026,937 A | 6/1991 | Bricker | |
| 5,030,782 A * | 7/1991 | Harandi et al. | 585/322 |
| 5,043,506 A | 8/1991 | Crossland | |
| 5,053,570 A | 10/1991 | Soto et al. | |
| 5,186,908 A | 2/1993 | Nemet-Mavrodin et al. | |
| 5,210,350 A | 5/1993 | Solofo et al. | |
| 5,215,950 A | 6/1993 | Bournonville et al. | |
| 5,227,557 A | 7/1993 | Bournonville et al. | 585/419 |
| 5,258,563 A | 11/1993 | Gosling et al. | |
| 5,258,564 A | 11/1993 | Kocal et al. | |
| 5,386,071 A | 1/1995 | Kuchar et al. | |
| 5,456,822 A | 10/1995 | Marcilly et al. | |
| 5,932,777 A | 8/1999 | Sughrue, II et al. | |
| 5,936,135 A | 8/1999 | Choudhary et al. | 585/418 |
| 6,143,941 A | 11/2000 | Sharma et al. | |
| 6,177,002 B1 | 1/2001 | Glover | |
| 6,552,243 B2 | 4/2003 | Allison et al. | 585/943 |
| 6,635,792 B2 | 10/2003 | Choi et al. | |
| 7,019,184 B2 | 3/2006 | Allison et al. | |
| 7,186,871 B2 | 3/2007 | Mitchell et al. | 585/418 |
| 7,186,872 B2 | 3/2007 | Juttu et al. | 585/419 |
| 7,276,636 B2 | 10/2007 | Jeanneret | 585/323 |
| 2003/0036670 A1 | 2/2003 | Oh et al. | |
| 2003/0135078 A1 | 7/2003 | Lattner et al. | |
| 2004/0020827 A1 | 2/2004 | Elomari | |
| 2004/0028584 A1 | 2/2004 | Jutta et al. | |
| 2005/0143610 A1 | 6/2005 | Mitchell et al. | |
| 2006/0287564 A1 | 12/2006 | Choi et al. | |
| 2007/0249879 A1 | 10/2007 | Iaccino et al. | |
| 2008/0093980 A1 | 4/2008 | Stoessel et al. | |
| 2009/0156870 A1 | 6/2009 | Lauritzen et al. | 585/24 |
| 2009/0209794 A1 | 8/2009 | Lauritzen et al. | 585/415 |
| 2009/0209795 A1 | 8/2009 | Lauritzen et al. | 585/417 |
| 2010/0048969 A1 | 2/2010 | Lauritzen et al. | 585/417 |
| 2011/0021853 A1 | 1/2011 | Lauritzen et al. | 585/417 |

FOREIGN PATENT DOCUMENTS

| | | | |
|---|---|---|---|
| CN | 85104308 | 12/1986 | |
| CN | 86104303 | 2/1987 | |
| CN | 1337890 | 2/2002 | |
| CN | 1342631 | 4/2002 | |
| CN | 1674988 | 9/2005 | |
| CN | 1902145 | 1/2007 | |
| EP | 0050021 | 4/1982 | |
| EP | 0130251 | 1/1985 | |
| EP | 0147111 | 7/1985 | C07C 2/76 |
| EP | 162636 | 11/1985 | |
| EP | 0244162 | 11/1987 | C07C 2/76 |
| EP | 0269297 | 6/1988 | |
| EP | 0493040 | 7/1992 | |
| EP | 0512912 | 11/1992 | |
| EP | 0905112 | 3/1999 | |
| EP | 1001001 | 5/2000 | |
| GB | 1442850 | 7/1976 | |
| RU | 2277524 | 12/2004 | |
| WO | 2007037866 | 4/2007 | |
| WO | 2007048853 | 5/2007 | |
| WO | 2007123977 | 11/2007 | |
| WO | 2007144324 | 12/2007 | |
| WO | 2009076393 | 6/2009 | |
| WO | 2009105391 | 8/2009 | |

OTHER PUBLICATIONS

Inui, T. et al., "Synthesis of Aromatic Hydrocarbons from Low-Grade Paraffins Using High-Silica Zeolite Catalysts and Metal Carriers", Chemistry Express vol. 1., pp. 53-56 (1986), Kinki Chemical Society, Japan.

Solymosi, F. et al., "Conversion of Ethane into Benzene on Mo2C/ZSM-5 Catalyst," Applied Catalysis A: General vol. 166, No. 1, 1998, pp. 225-235.

* cited by examiner

PROCESS FOR THE CONVERSION OF MIXED LOWER ALKANES TO AROMATIC HYDROCARBONS

PRIORITY CLAIM

The present application claims priority from PCT/US2010/054600, filed 29 Oct. 2010, which claims priority from 61/257,085, filed 2 Nov. 2009.

FIELD OF THE INVENTION

The present invention relates to a process for producing aromatic hydrocarbons from mixed lower alkanes. More specifically, the invention relates to a two stage process for increasing the production of benzene from a mixture of ethane and propane or ethane, propane and butane in a dehydroaromatization process.

BACKGROUND OF THE INVENTION

There is a projected global shortage for benzene which is needed in the manufacture of key petrochemicals such as styrene, phenol, nylon and polyurethanes, among others. Generally, benzene and other aromatic hydrocarbons are obtained by separating a feedstock fraction which is rich in aromatic compounds, such as reformate produced through a catalytic reforming process and pyrolysis gasolines produced through a naphtha cracking process, from non-aromatic hydrocarbons using a solvent extraction process.

To meet this projected supply shortage, numerous catalysts and processes for on-purpose production of aromatics (including benzene) from alkanes containing six or less carbon atoms per molecule have been investigated. These catalysts are usually bifunctional, containing a zeolite or molecular sieve material to provide acidity and one or more metals such as Pt, Ga, Zn, Mo, etc. to provide dehydrogenation activity. For example, U.S. Pat. No. 4,350,835 describes a process for converting ethane-containing gaseous feeds to aromatics using a crystalline zeolite catalyst of the ZSM-5-type family containing a minor amount of Ga. As another example, U.S. Pat. No. 7,186,871 describes aromatization of $C_1$-$C_4$ alkanes using a catalyst containing Pt and ZSM-5.

Most lower alkane dehydroaromatization processes carry out the reaction in one step. For example, EP0147111 describes an aromatization process wherein a $C_3$-$C_4$ feed is mixed with ethane and all are reacted together in a single reactor. A minority of these processes involves two separate steps or stages. For example, U.S. Pat. No. 3,827,968 describes a process which involves oligomerization followed by aromatization. U.S. Pat. No. 4,554,393 and U.S. Pat. No. 4,861,932 describe two-step processes for propane involving dehydrogenation followed by aromatization. None of these examples mention a two-stage process in which lower alkane aromatization takes place in both stages.

The ease of conversion of individual alkanes to aromatics increases with increasing carbon number. When a mixed feed consisting of ethane and higher hydrocarbons is converted into benzene plus higher aromatics in a single stage, the selection of reaction severity is dictated by the desired overall hydrocarbon conversion target. If a significant level of ethane conversion is desired or needed, this may lead to operating such a one-stage process at higher temperature severity. The negative consequence of this higher severity is such that higher hydrocarbons such as propane can undergo non-selective side reactions which result in excessive hydrogenolysis into lower-valued methane. The net result is that the overall yield to benzene and other aromatics is reduced significantly.

It would be advantageous to provide a light alkane dehydroaromatization process wherein (a) the conversion of each component of a mixed alkane feed can be optimized, (b) the ultimate yield of benzene is greater than that of any other single aromatic product, and (c) the generation of undesired methane by-product is minimized.

SUMMARY OF THE INVENTION

The above problem is resolved according to the present invention by de-coupling the severity which is optimal for propane from that which is optimal for ethane. This is accomplished by designing a two-stage process as described below.

The present invention provides a process for the conversion of mixed lower alkanes into aromatics which comprises first reacting a mixed lower alkane feed comprising at least propane and ethane in the presence of an aromatization catalyst under first stage reaction conditions which maximize the conversion of propane (and, optionally, any higher hydrocarbons such as butane which may be present in the feed) into first stage aromatic reaction products, separating the first aromatic reaction products from unreacted ethane (and, optionally, any other non-aromatic hydrocarbons, including ethane, which may be produced in the reaction), reacting ethane (and, optionally, at least a portion of the any other non-aromatic hydrocarbons) in the presence of an aromatization catalyst under second stage reaction conditions which maximize the conversion of ethane (and, optionally, any other non-aromatic hydrocarbons which may be produced in the first stage) into second stage aromatic reaction products, and optionally separating ethane (and any other non-aromatic hydrocarbons which may be produced) from the second aromatic reaction products.

Fuel gas, which includes primarily methane and hydrogen, may also be produced in either or both of the first and second stages. The fuel gas may be separated from the aromatic reaction products in either or both of the stages. Thus, fuel gas may be an additional product of the process of this invention.

DETAILED DESCRIPTION OF THE INVENTION

The present invention is a process for producing aromatic hydrocarbons which comprises bringing into contact a hydrocarbon feedstock containing at least propane and ethane, preferably at least 20 wt % ethane and at least 20 wt % propane, and possibly other hydrocarbons such as butane, and a catalyst composition suitable for promoting the reaction of such hydrocarbons to aromatic hydrocarbons, such as benzene, at a temperature of from about 400 to about 700° C. and a pressure of from about 0.01 to about 1.0 Mpa absolute. The gas hourly space velocity (GHSV) per hour may range from about 300 to about 6000. These conditions are used in each of the stages but the conditions in the stages may be the same or different. The conditions may be optimized for the conversion of propane, and possibly other higher alkanes such as butane, in the first stage and ethane in the second stage. In the first stage, the reaction temperature preferably ranges from about 400 to about 650° C., most preferably from about 420 to about 650° C., and in the second stage, the reaction temperature preferably ranges from about 450 to about 680° C., most preferably from about 450 to about 660° C. The primary desired products of the process of this invention are benzene, toluene and xylene (BTX). In an embodiment, the first stage reaction conditions may be optimized for the conversion to BTX of propane. Optionally, the first stage reaction conditions may also be optimized for the conversion to BTX of any higher hydrocarbons which may be present in the feedstock. In another embodiment, the second stage reaction conditions may be optimized for the conversion to BTX of ethane. Optionally, the second stage reaction conditions may also be optimized for the conversion to BTX of any other non-aromatic hydrocarbons which may be produced in the first stage.

The first stage and second stage reactors may be operated under similar conditions. When either reactor is run at higher temperatures, i.e., above about 630-650° C., more fuel gas and less aromatics are produced even though the net feed conversion per pass for that stage may be higher. Therefore it is better to run at lower temperature and convert less feed in each pass of each stage in order to produce more aromatics in total even though more ethane will have to be recycled. Operating in the preferred range helps to maximize aromatics production by minimizing fuel gas production. The use of higher temperatures may maximize the production of fuel gas.

Fuel gas may be an additional product of the process of the present invention. Fuel gas includes primarily methane and hydrogen which are produced along with the aromatics. Fuel gas may be used for power and/or steam generation. The hydrogen in the fuel gas may be separated and used for refinery or chemical reactions that require hydrogen, including the hydrodealkylation of toluene and/or xylene as discussed below.

It is possible to carry out this process in batch mode using separate reactors for each stage or using the same reactor for each stage but it is highly preferred that it be carried out in continuous mode in separate reactors. Each stage may be carried out in a single reactor or in two or more reactors aligned in parallel. Preferably, at least two reactors are used in each stage so that one reactor may be in use for aromatization while the other reactor is offline so the catalyst may be regenerated. The aromatization reactor system may be a fluidized bed, moving bed or a cyclic fixed bed design. The cyclic fixed bed design is preferred for use in this invention.

The hydrocarbons in the feedstock may be comprised of at least about 20 wt % of propane, at least about 20 wt % of ethane, and, optionally, at least about 10 to 20 wt % of butane, pentane, etc. In one embodiment, the feedstock is from about 30 to about 50 wt % propane and from about 30 to about 50 wt % ethane. The feed may contain small amounts of $C_2$-$C_4$ olefins, preferably no more than 5 to 10 weight percent. Too much olefin may cause an unacceptable amount of coking and deactivation of the catalyst.

A mixed propane/ethane or mixed $C_2$-$C_4$ lower alkane feed stream may be derived from, for example, an ethane/propane-rich stream derived from natural gas, refinery or petrochemical streams including waste streams. Examples of potentially suitable feed streams include (but are not limited to) residual ethane and propane and butane from natural gas (methane) purification, pure ethane and propane and butane streams (also known as Natural Gas Liquids) co-produced at a liquefied natural gas (LNG) site, $C_2$-$C_4$ streams from associated gases co-produced with crude oil production (which are usually too small to justify building a LNG plant but may be sufficient for a chemical plant), unreacted "waste" streams from steam crackers, and the $C_1$-$C_4$ byproduct stream from naphtha reformers (the latter two are of low value in some markets such as the Middle East).

Usually natural gas, comprising predominantly methane, enters an LNG plant at elevated pressures and is pre-treated to produce a purified feed stock suitable for liquefaction at cryogenic temperatures. Ethane, propane, butane and other gases are separated from the methane. The purified gas (methane) is processed through a plurality of cooling stages using heat exchangers to progressively reduce its temperature until liquefaction is achieved. The separated gases may be used as the feed stream of the present invention. The byproduct streams produced by the process of the present invention may have to be cooled for storage or recycle and the cooling may be carried out using the heat exchangers used for the cooling of the purified methane gas.

Any one of a variety of catalysts may be used to promote the reaction of propane and ethane and possibly other alkanes to aromatic hydrocarbons. One such catalyst is described in U.S. Pat. No. 4,899,006 which is herein incorporated by reference in its entirety. The catalyst composition described therein comprises an aluminosilicate having gallium deposited thereon and/or an aluminosilicate in which cations have been exchanged with gallium ions. The molar ratio of silica to alumina is at least 5:1.

Another catalyst which may be used in the process of the present invention is described in EP 0 244 162. This catalyst comprises the catalyst described in the preceding paragraph and a Group VIII metal selected from rhodium and platinum. The aluminosilicates are said to preferably be MFI or MEL type structures and may be ZSM-5, ZSM-8, ZSM-11, ZSM-12 or ZSM-35.

Other catalysts which may be used in the process of the present invention are described in U.S. Pat. No. 7,186,871 and U.S. Pat. No. 7,186,872, both of which are herein incorporated by reference in their entirety. The first of these patents describes a platinum containing ZSM-5 crystalline zeolite synthesized by preparing the zeolite containing the aluminum and silicon in the framework, depositing platinum on the zeolite and calcining the zeolite. The second patent describes such a catalyst which contains gallium in the framework and is essentially aluminum-free.

It is preferred that the catalyst be comprised of a zeolite, a noble metal of the platinum family to promote the dehydrogenation reaction, and a second inert or less active metal which will attenuate the tendency of the noble metal to catalyze hydrogenolysis of the $C_2$ and higher hydrocarbons in the feed to methane and/or ethane. Attenuating metals which can be used include those described below.

Additional catalysts which may be used in the process of the present invention include those described in U.S. Pat. No. 5,227,557, hereby incorporated by reference in its entirety. These catalysts contain an MFI zeolite plus at least one noble metal from the platinum family and at least one additional metal chosen from the group consisting of tin, germanium, lead, and indium.

One preferred catalyst for use in this invention is described in U.S. application Ser. No. 12/371,787, filed Feb. 16, 2009 entitled "Process for the Conversion of Ethane to Aromatic Hydrocarbons." This application is hereby incorporated by reference in its entirety. This application describes a catalyst comprising: (1) 0.005 to 0.1 wt % (% by weight) platinum, based on the metal, preferably 0.01 to 0.05 wt %, (2) an amount of an attenuating metal selected from the group consisting of tin, lead, and germanium which is preferably not more than 0.2 wt % of the catalyst, based on the metal and wherein the amount of platinum may be no more than 0.02 wt % more than the amount of the attenuating metal; (3) 10 to 99.9 wt % of an aluminosilicate, preferably a zeolite, based on the aluminosilicate, preferably 30 to 99.9 wt %, preferably selected from the group consisting of ZSM-5, ZSM-11, ZSM-12, ZSM-23, or ZSM-35, preferably converted to the H+ form, preferably having a $SiO_2/Al_2O_3$ molar ratio of from 20:1 to 80:1, and (4) a binder, preferably selected from silica, alumina and mixtures thereof.

Another preferred catalyst for use in this invention is described in U.S. Provisional Application No. 61/029,939, filed Feb. 20, 2008 entitled "Process for the Conversion of Ethane to Aromatic Hydrocarbons." This application is hereby incorporated by reference in its entirety. The application describes a catalyst comprising: (1) 0.005 to 0.1 wt % (% by weight) platinum, based on the metal, preferably 0.01 to 0.06 wt %, most preferably 0.01 to 0.05 wt %, (2) an amount of iron which is equal to or greater than the amount of the platinum but not more than 0.50 wt % of the catalyst, preferably not more than 0.20 wt % of the catalyst, most preferably not more than 0.10 wt % of the catalyst, based on the metal; (3) 10 to 99.9 wt % of an aluminosilicate, preferably a zeolite, based on the aluminosilicate, preferably 30 to 99.9 wt %, preferably selected from the group consisting of ZSM-5, ZSM-11, ZSM-12, ZSM-23, or ZSM-35, preferably converted to the H+ form, preferably having a $SiO_2/Al_2O_3$ molar ratio of from 20:1 to 80:1, and (4) a binder, preferably selected from silica, alumina and mixtures thereof.

Another preferred catalyst for use in this invention is described in U.S. patent application Ser. No. 12/371,803, filed Feb. 16, 2009 entitled "Process for the Conversion of Ethane to Aromatic Hydrocarbons." This application is hereby incorporated by reference in its entirety. This application describes a catalyst comprising: (1) 0.005 to 0.1 wt % (% by weight) platinum, based on the metal, preferably 0.01 to 0.05% wt, most preferably 0.02 to 0.05% wt, (2) an amount of gallium which is equal to or greater than the amount of the platinum, preferably no more than 1 wt %, most preferably no more than 0.5 wt %, based on the metal; (3) 10 to 99.9 wt % of an aluminosilicate, preferably a zeolite, based on the aluminosilicate, preferably 30 to 99.9 wt %, preferably selected from the group consisting of ZSM-5, ZSM-11, ZSM-12, ZSM-23, or ZSM-35, preferably converted to the H+ form, preferably having a $SiO_2/Al_2O_3$ molar ratio of from 20:1 to 80:1, and (4) a binder, preferably selected from silica, alumina and mixtures thereof.

One of the undesirable products of the aromatization reaction is coke which may deactivate the catalyst. While catalysts and operating conditions and reactors are chosen to minimize the production of coke, it is usually necessary to regenerate the catalyst at some time during its useful life. Regeneration may increase the useful life of the catalyst.

Regeneration of coked catalysts has been practiced commercially for decades and various regeneration methods are known to those skilled in the art.

The regeneration of the catalyst may be carried out in the aromatization reactor or in a separate regeneration vessel or reactor. For example, the catalyst may be regenerated by burning the coke at high temperature in the presence of an oxygen-containing gas as described in U.S. Pat. No. 4,795,845 which is herein incorporated by reference in its entirety. Regeneration with air and nitrogen is shown in the examples of U.S. Pat. No. 4,613,716 which is herein incorporated by reference in its entirety. Another possible method involves air calcination, hydrogen reduction, and treatment with sulfur or a sulfurization material. Platinum catalysts have been used to assist the combustion of coke deposited on such catalysts.

The preferred regeneration temperature range for use herein is from about 450 to about 788° C. The preferred temperature range for regeneration in the first stage is from about 470 to about 788° C. The preferred temperature range for regeneration in the second stage is from about 500 to about 788° C.

The unreacted methane and byproduct hydrocarbons may be used in other steps, stored and/or recycled. It may be necessary to cool these byproducts to liquefy them. When the ethane or mixed lower alkanes originate from an LNG plant as a result of the purification of the natural gas, at least some of these byproducts may be cooled and liquefied using the heat exchangers used to liquefy the purified natural gas (methane).

The toluene and xylene may be converted into benzene by hydrodealkylation. The hydrodealkylation reaction involves the reaction of toluene, xylenes, ethylbenzene, and higher aromatics with hydrogen to strip alkyl groups from the aromatic ring to produce additional benzene and light ends including methane and ethane which are separated from the benzene. This step substantially increases the overall yield of benzene and thus is highly advantageous.

Both thermal and catalytic hydrodealkylation processes are known in the art. Methods for hydrodealkylation are described in US Published Patent Application No. 2009/0156870 which is herein incorporated by reference in its entirety. The integrated process of this invention may also include the reaction of benzene with propylene to produce cumene which may in turn be converted into phenol and/or acetone. The propylene may be produced separately in a propane dehydrogenation unit or may come from olefin cracker process vent streams or other sources. Methods for the reaction of benzene with propylene to produce cumene are described in US Published Patent Application No. 2009/0156870 which is herein incorporated by reference in its entirety.

The integrated process of this invention may also include the reaction of benzene with olefins such as ethylene. The ethylene may be produced separately in an ethane dehydrogenation unit or may come from olefin cracker process vent streams or other sources. Ethylbenzene is an organic chemical compound which is an aromatic hydrocarbon. Its major use is in the petrochemical industry as an intermediate compound for the production of styrene, which in turn is used for making polystyrene, a commonly used plastic material. Methods for the reaction of benzene with ethylene to produce ethylbenzene are described in US Published Patent Application No. 2009/0156870 which is herein incorporated by reference in its entirety.

Styrene may then be produced by dehydrogenating the ethylbenzene. One process for producing styrene is described in U.S. Pat. No. 4,857,498, which is herein incorporated by reference in its entirety. Another process for producing styrene is described in U.S. Pat. No. 7,276,636, which is herein incorporated by reference in its entirety.

EXAMPLES

The following examples are provided for illustrative purposes only and are not intended to limit the scope of the invention.

Example 1

In this example the results of laboratory tests are used to represent a one-stage aromatization process vs. a two-stage process utilizing the same catalyst in each stage. The lower alkane feedstock of this example consists of 50 wt % each of ethane and propane, and the temperature of the second stage is higher than the temperature of the first stage.

Catalyst A was made on 1.6 mm diameter cylindrical extrudate particles containing 80 wt % of zeolite ZSM-5 CBV 2314 powder (23:1 molar $SiO_2/Al_2O_3$ ratio, available from Zeolyst International) and 20 wt % alumina binder. The extrudate samples were calcined in air up to 650° C. to remove residual moisture prior to use in catalyst preparation. The target metal loadings for Catalyst A were 0.025% w Pt and 0.09 wt % Ga.

Metals were deposited on 25-100 gram samples of the above ZSM-5/alumina extrudate by first combining appropriate amounts of stock aqueous solutions of tetraammine platinum nitrate and gallium(III) nitrate, diluting this mixture with deionized water to a volume just sufficient to fill the pores of the extrudate, and impregnating the extrudate with this solution at room temperature and atmospheric pressure. Impregnated samples were aged at room temperature for 2-3 hours and then dried overnight at 100° C.

Catalyst A was subjected to three performance tests as described below. Performance Test 1 was conducted under conditions which might be used for a one-stage aromatization process with a mixed ethane/propane feed. Performance Tests 2 and 3 were conducted under conditions which might be used for the first and second stages, respectively, of a two-stage aromatization process according to the present invention.

For each of the three performance tests, a 15-cc charge of fresh (not previously tested) catalyst was loaded "as is," without crushing, into a Type 316H stainless steel tube (1.40 cm i.d.) and positioned in a four-zone furnace connected to a gas flow system.

Prior to Performance Test 1, the fresh charge of Catalyst A was pretreated in situ at atmospheric pressure (ca. 0.1 MPa absolute) as follows:

(a) calcination with air at approximately 60 liters per hour (L/hr), during which the reactor wall temperature was raised from 25 to 510° C. in 12 hrs, held at 510° C. for 4-8 hrs, then further increased from 510° C. to 630° C. in 1 hr, then held at 630° C. for 30 min;

(b) nitrogen purge at approximately 60 L/hr, 630° C., for 20 min;

(c) reduction with hydrogen at 60 L/hr, for 30 min, during which time the reactor wall temperature was raised from 630° C. to 675° C.

At the end of the above reduction step, the hydrogen flow was terminated, and the catalyst charge was exposed to a feed consisting of 50 wt % ethane and 50 wt % propane at atmospheric pressure (ca. 0.1 MPa absolute), 675° C. reactor wall temperature, and a feed rate of 1000 GHSV (1000 cc feed per cc of catalyst per hr). Three minutes after introduction of the feed, the total reactor outlet stream was sampled by an online gas chromatograph for analysis. Based on composition data obtained from the gas chromatographic analysis, initial ethane, propane, and total conversions were computed according to the following formulas:

Ethane conversion, %=100×(wt % ethane in feed−wt % ethane in outlet stream)/(wt % ethane in feed)

Propane conversion, %=100×(wt % propane in feed−wt % propane in outlet stream)/(wt % propane in feed)

Total ethane+propane conversion=((wt % ethane in feed×% ethane conversion)+(wt % propane in feed×% propane conversion))/100

Performance Test 2 was conducted in the same manner and under the same conditions as Performance Test 1 above, except that the final temperature reached during the air calcination pretreatment step was 600° C., the nitrogen purge and hydrogen reduction steps were conducted at 600° C., and the ethane/propane feed was introduced at 600° C. reactor wall temperature. This simulates the first stage of a two stage process.

For Performance Test 3, the fresh charge of Catalyst A was pretreated in situ at atmospheric pressure (ca. 0.1 MPa absolute) as follows:

(a) calcination with air at approximately 60 liters per hour (L/hr), during which the reactor wall temperature was raised from 25 to 510° C. in 12 hrs, then held at 510° C. for 4-8 hrs;

(b) nitrogen purge at approximately 60 L/hr, 510° C., for 30 min;

(c) reduction with hydrogen at 60 L/hr, for 2 hrs.

At the end of the above reduction step, the hydrogen flow was terminated, and the catalyst charge was exposed to a feed consisting of 100 wt % ethane at atmospheric pressure (ca. 0.1 MPa absolute), 510° C. reactor wall temperature, and a feed rate of 1000 GHSV (1000 cc feed per cc of catalyst per hr). After 10 min at these conditions, the reactor wall temperature was raised to 621° C. At 25 min after introduction of the ethane feed, the total reactor outlet stream was sampled by an online gas chromatograph for analysis. Based on composition data obtained from the gas chromatographic analysis, initial ethane, propane, and total conversions were computed according to the formulas given above.

Table 1 lists the results of online gas chromatographic analyses of the total product streams from Performance Tests 1-3 described above.

TABLE 1

| PERFORMANCE TEST | 1 | 2 | 3 |
|---|---|---|---|
| Catalyst | A | A | A |
| Catalyst volume, cc | 15 | 15 | 15 |
| Reactor wall temperature, ° C. | 675 | 600 | 621 |
| Pressure, MPa | 0.1 | 0.1 | 0.1 |
| Feed composition | | | |
| Ethane, wt % | 50 | 50 | 100 |
| Propane, wt % | 50 | 50 | -0- |
| Total feed rate, GHSV | 1000 | 1000 | 1000 |
| Total feed rate, WHSV | 1.93 | 1.88 | 1.61 |
| Ethane conversion, % | 51.50 | 1.10 | 49.28 |
| Propane conversion, % | 99.50 | 98.62 | — |
| Total ethane + propane conversion, % | 75.49 | 49.84 | 49.28 |
| Reactor outlet composition, wt % | | | |
| Hydrogen | 5.43 | 3.44 | 4.71 |
| Methane | 17.33 | 9.91 | 7.56 |
| Ethylene | 5.51 | 2.81 | 3.95 |
| Ethane | 24.26 | 49.47 | 50.72 |
| Propylene | 0.59 | 0.42 | 0.58 |
| Propane | 0.25 | 0.69 | 0.70 |
| C4 | 0.09 | 0.08 | 0.11 |
| C5 | -0- | -0- | -0- |
| Benzene | 26.64 | 18.40 | 16.60 |
| Toluene | 10.21 | 11.77 | 8.72 |
| C8 aromatics | 1.47 | 2.67 | 1.70 |
| C9+ aromatics | 8.22 | 0.34 | 4.65 |
| Total aromatics | 46.54 | 33.18 | 31.67 |

From Table 1, it can be seen that the one stage method produced 46.54 wt % total aromatics from the given ethane/propane feedstock, while the two stage method produced 48.85 wt % total aromatics based on a 100 wt % total feed to stage 1 followed by stage 2 which is fed with the unconverted ethane from stage 1. In a true two stage operation, it is likely that the feed to stage 2 would include all non-aromatics from the outlet of stage 1 except the fuel gas (methane and hydrogen). These non-aromatics would include not only unconverted ethane but also ethylene, propylene, propane, etc. which would likely increase the total aromatics yield to slightly more than 50 wt % based on a 100 wt % total feed to stage 1.

Example 2

Process Configuration Comparisons 2.1 One-Stage Process (Comparative)

Figure 1:
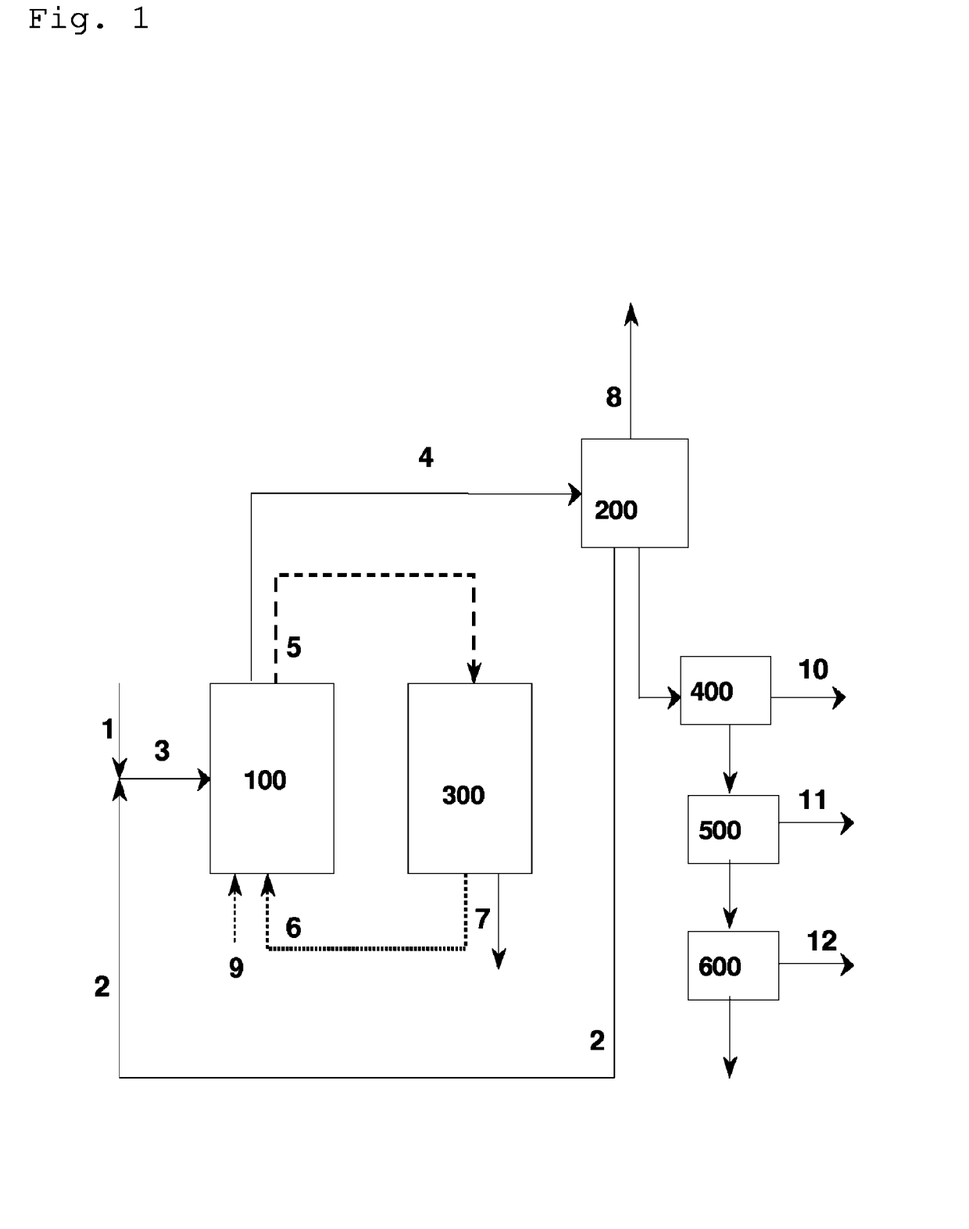
FIG. 1 is a schematic flow diagram which illustrates the process scheme for producing aromatics (benzene and higher aromatics) from a mixed lower alkane feed containing at least ethane and propane using a one reactor-regenerator stage process.

FIG. 1 is a schematic flow diagram, which illustrates the process scheme for producing aromatics (benzene and higher aromatics) from a feed containing 50 wt % ethane and 50 wt % propane using a one reactor-regenerator stage process.

25 tonnes/hr (tph) of stream 1, which constitutes primarily 50/50 (ethane/propane) mixed feed (including minor amounts of methane, butane, etc.) is mixed with a recycle stream 2 that consists primarily of ethane and other hydrocarbons, possibly including but not limited to, ethylene, propane, propylene, methane, butane and some hydrogen. The total feed stream 3 is now introduced to the single stage aromatization reactor 100. The aromatization reactor system may be a fluidized bed, moving bed or a cyclic fixed bed design. Here the cyclic fixed bed design is used. The reactor system employs "Catalyst A" described in example 1 above. The unconverted reactants as well as the products leave the reactor 100 via stream 4 and are fed to the separation system. The unconverted reactants and light hydrocarbons are recycled back in stream 2 to the reactor 100 while the separation system yields fuel gas (predominantly methane and hydrogen in stream 8 from vapor-liquid separator 200), $C_{9+}$ liquid products and benzene, toluene and xylenes (BTX).

The reactor 100 operates at about 1 atmosphere pressure and at a temperature of 675° C. while the regenerator 300, to which the coke formed in reactor 100 is removed, operates at around 730° C. The heat (9) required for the reaction step is provided by the hot catalyst solid mixture which is preheated during the regeneration step. In the regeneration step, catalyst containing coke flows through stream 5 to regenerator 300 and stripping gas is supplied. Regenerated catalyst flows back to the reactor 100 through stream 6 and the stripping gas exits the regenerator 300 through stream 7.

The reactor 100 achieves almost complete conversion of propane (greater than 99%) while converting about half the ethane as was the case in performance test 1 in Tables 1 and above. The average single pass mixed feed conversion is 75.49%. The liquid products are separated in a sequence of three consecutive columns to obtain the separated liquid products as shown in FIG. 1. The process yields are summarized in Table 2 below. This one stage mode of operation produces about 8.33 tph of benzene (from column 400 through stream 10), 3.25 tph toluene (from column 500 through stream 11) and 0.5 tph of mixed xylenes (from column 600 through stream 12) resulting in an overall BTX yield of 49 wt %, an overall liquid yield of 60 wt % with respect to the mixed feed. The fuel gas make (stream 8) is 9.2 tph which is about 36.7 wt % of the mixed feed.

2.2 Two-Stage Process

Figure 2:
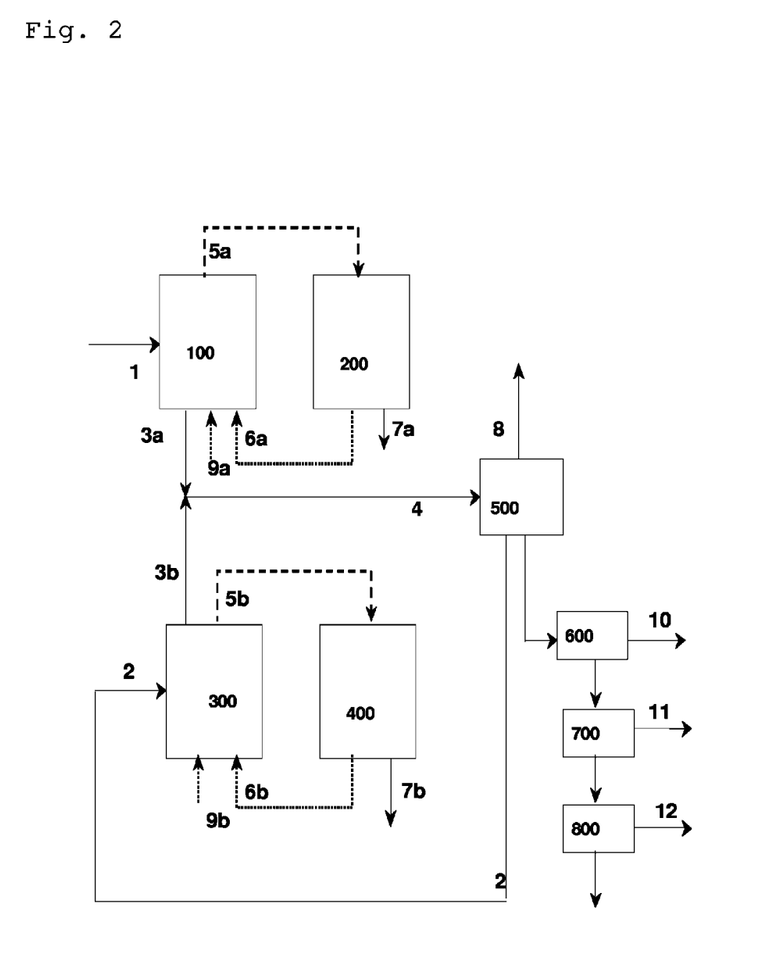
FIG. 2 is a schematic flow diagram for producing aromatics (benzene and higher aromatics) from a mixed lower alkane feed containing at least ethane and propane using a two stage reactor-regenerator system.

FIG. 2 is a schematic flow diagram for producing aromatics (benzene and higher aromatics) from a feed containing 50 wt % ethane and 50 wt % propane using a two stage reactor-regenerator system according to the present invention.

25 tonnes/hr (tph) of primarily of 50/50 ethane/propane mixed feed, including minor amounts of methane, butane, etc. (stream 1) are fed to the stage 1 aromatization reactor 100 that uses "Catalyst A" described in example 1. The first stage reactor 100 operates at about 1 atmosphere pressure and at a temperature of about 600° C. while the stage 1 regenerator 200, which removes the coke formed in the reactor 100, operates at around 730° C. The heat required for the reaction step is provided by the hot catalyst solid mixture which is preheated during the regeneration step. The reactor 100 achieves almost complete conversion of propane (greater than 98%) with minimal ethane conversion as was the case in performance test 2 in Table 1. The reactor effluent stream 3a is then mixed with the reactor effluent from the second stage reactor 300 (stream 3b), described below. The combined effluent from both the reactor stages (stream 4) is then fed to a separation system where unconverted reactants and light hydrocarbons that consist primarily of ethane and some other hydrocarbons, which may include ethylene, propane, propylene, methane, butane and some hydrogen, are used as the feed (stream 2) for the stage-2 aromatization reactor 300 which uses "catalyst A" described above.

The second stage reactor 300 operates at about 1 atmosphere pressure and a temperature of about 620° C. while the regenerator 400, which removes the coke formed in the reactor, operates at around 730° C. The heat required for the reaction step is provided by the hot catalyst solid mixture which is preheated during the regeneration step. The second stage reactor 300 converts almost half the ethane fed to it as was the case in performance test 3 in Table 1 above. The effluent from the second stage reactor 300 (stream 3b) is mixed with the effluent from the first stage reactor 100 as described above. Both stage-1 and stage-2 of the aromatization reactor system use a cyclic fixed bed design.

The average single pass conversion for the mixed feed is obtained from the cumulative conversion of ethane and propane (feeds) over both the stages and is calculated to be 74.5%. The liquid products are separated in a sequence of three consecutive columns to obtain the separated liquid products as shown in FIG. 2. The process yields are summarized in Table 3 below. This two-stage mode of operation produces about 8.6 tph of benzene (from column 600 through stream 10), 5.1 tph toluene (from column 700 through stream 11) and 1.1 tph xylenes (from column 800 through stream 12) resulting in an overall BTX yield of 60 wt % and an overall liquid yield of 65 wt % with respect to the mixed feed. The undesired fuel gas make (stream 8 from vapor-liquid separator 500) is about 7 tph which is about 28 wt % of the mixed feed.

2.3 Comparison of Process Configurations

Table 2 below shows the comparison of the system performance for one stage and two stage processes. The processes are compared for conditions resulting in constant overall feed conversions. The single stage process has to be operated at higher temperature as compared to each of the two stages in the two-stage process to achieve a similar feed conversion per pass. It is evident from Table 2 that the two-stage operation results in better product yields of benzene, toluene, mixed xylenes and $C_{9+}$ liquids with lower undesired fuel gas make as compared to the one stage process.

TABLE 2

| Feed (ethane/propane) | 50-50 (wt %) | 50-50 (wt %) |
|---|---|---|
| Reactor (stages) | One stage | Two stages |
| Catalyst | A (stage 1) | A (stage 1) |
|  |  | A (stage 2) |
| Average conversion per pass | 75.5 | 74.5 |

TABLE 2-continued

| Feed (ethane/propane)<br>Reactor (stages) | 50-50 (wt %)<br>One stage | 50-50 (wt %)<br>Two stages |
|---|---|---|
| GHSV (per hr) | 1000 | 1000 (both stages) |
| Reactor Temp (° C.) | Stage-1: 675 | Stage-1: 600 |
|  |  | Stage-2: 621 |
| Benzene yield<br>(tonne/tonne$_{feed}$, %) | 33.3% | 34.4% |
| Toluene yield<br>(tonne/tonne$_{feed}$, %) | 13.0% | 20.4% |
| Mixed Xylene yield<br>(tonne/tonne$_{feed}$, %) | 2.0% | 4.4% |
| C9+ liquids yield<br>(tonne/tonne$_{feed}$, %) | 10.33% | 5.2% |
| Total BTX yield<br>(tonne/tonne$_{feed}$, %) | 48.3% | 59.2% |
| Total Liq yield<br>(tonne/tonne$_{feed}$, %) | 58.7% | 64.4% |
| Total fuel-gas make<br>(tonne/tonne$_{feed}$, %) | 36.7% | 28% |

Note:
All yields are expressed as tonnes of the product per tonne of the mixed feed entering the overall process, expressed as percentage.
The average conversion per pass for a two-stage process is computed as: (Total propane conversion × mol fraction of propane in the mixed feed) + (Total ethane conversion × mol fraction of ethane in the mixed feed)

Example 3

In this example the results of laboratory tests are used to represent a one-stage aromatization process vs. a two-stage process utilizing the different catalysts in each stage. The lower alkane feedstock of this example consists of 50 wt % each of ethane and propane, and the temperature of the second stage is higher than the temperature of the first stage.

Catalyst B was prepared on a sample of zeolite ZSM-5 CBV 3024E powder (30:1 molar SiO$_2$/Al$_2$O$_3$ ratio), available from Zeolyst International. The ZSM-5 powder sample was calcined in air up to 650° C. to remove residual moisture prior to use in catalyst preparation. The target metal loadings for Catalyst B were 0.04 wt % each of platinum and tin.

Metals were deposited on a 50-gram sample of the above ZSM-5 powder by first combining appropriate amounts of stock aqueous solutions of tetraammine platinum nitrate and tin(IV) tetrachloride pentahydrate, diluting this mixture with deionized water to a volume just sufficient to fill the pores of the powder, and impregnating the powder with this solution at room temperature and atmospheric pressure. The impregnated sample was aged at room temperature for approximately 2 hrs, then dried overnight at 100° C.

The dried catalyst powder was loaded into plastic bags and pressed at 1380 barg for 2 min using an isostatic press. The resulting "rock" was then crushed and sieved to obtain 2.5-8.5 mm particles suitable for performance testing.

For Performance Test 4, a 15-cc charge of fresh (not previously tested), pressed and crushed Catalyst B was loaded into a Type 316H stainless steel tube (1.40 cm i.d.) and positioned in a four-zone furnace connected to a gas flow system. Performance Test 4 was conducted in the same manner and under the same conditions as Performance Test 3 in Example 1 above. Based on composition data obtained from the gas chromatographic analysis, initial ethane, propane, and total conversions were computed according to the formulas given above for Example 1.

Table 3 lists the results of online gas chromatographic analyses of the total product streams from Performance Tests 1 and 2 (from Example 1) and Performance Test 4. Performance Test 1 was conducted under conditions which might be used for a one-stage aromatization process with a mixed ethane/propane feed. Performance Tests 2 and 4 were conducted under conditions which might be used for the first and second stages, respectively, of a two-stage aromatization process according to the present invention.

TABLE 3

| PERFORMANCE TEST | 1 | 2 | 4 |
|---|---|---|---|
| Catalyst | A | A | B |
| Catalyst volume, cc | 15 | 15 | 15 |
| Reactor wall temperature, ° C. | 675 | 600 | 621 |
| Pressure, MPa | 0.1 | 0.1 | 0.1 |
| Feed composition |  |  |  |
| Ethane, wt % | 50 | 50 | 100 |
| Propane, wt % | 50 | 50 | -0- |
| Total feed rate, GHSV | 1000 | 1000 | 1000 |
| Total feed rate, WHSV | 1.93 | 1.88 | 2.05 |
| Ethane conversion, % | 51.50 | 1.10 | 50.97 |
| Propane conversion, % | 99.50 | 98.62 | — |
| Total ethane + propane conversion, % | 75.49 | 49.84 | 50.97 |
| Reactor outlet composition, wt % |  |  |  |
| Hydrogen | 5.43 | 3.44 | 4.78 |
| Methane | 17.33 | 9.91 | 8.48 |
| Ethylene | 5.51 | 2.81 | 4.23 |
| Ethane | 24.26 | 49.47 | 49.03 |
| Propylene | 0.59 | 0.42 | 0.54 |
| Propane | 0.25 | 0.69 | 0.60 |
| C4 | 0.09 | 0.08 | 0.10 |
| C5 | -0- | -0- | 0.01 |
| Benzene | 26.64 | 18.40 | 15.19 |
| Toluene | 10.21 | 11.77 | 8.93 |
| C8 aromatics | 1.47 | 2.67 | 1.93 |
| C9+ aromatics | 8.22 | 0.34 | 6.19 |
| Total aromatics | 46.54 | 33.18 | 32.24 |

From Table 3 it can be seen that the one stage method produced 46.54 wt % total aromatics from the given ethane/propane feedstock, while the two stage method produced 49.13 wt % total aromatics based on a 100 wt % total feed to stage 1 followed by stage 2 which is fed with the unconverted ethane from stage 1. In a true two stage operation, it is likely that the feed to stage 2 would include all non-aromatics from the outlet of stage 1 except the fuel gas (methane and hydrogen). These non-aromatics would include not only unconverted ethane but also ethylene, propylene, propane, etc. which would likely increase the total aromatics yield to slightly more than 50 wt % based on a 100 wt % total feed to stage 1.

Example 4

Process Configuration Comparisons 4.1 One-Stage Process (Comparative)

FIG. 1 is a schematic flow diagram, which illustrates the process scheme for producing aromatics (benzene and higher aromatics) from a feed containing 50 wt % ethane and 50 wt % propane using a one reactor-regenerator stage process.

25 tonnes/hr (tph) of stream 1, which constitutes primarily 50/50 (ethane/propane) mixed feed, (including minor amounts of methane, butane, etc.) is mixed with a recycle stream 2 that consists primarily of ethane and other hydrocarbons, possibly including but not limited to, ethylene, propane, propylene, methane, butane and some hydrogen. The total feed stream 3 is now introduced to the single stage aromatization reactor 100. The aromatization reactor system may be a fluidized bed, moving bed or a cyclic fixed bed design. Here the cyclic fixed bed design is used. The reactor system employs "Catalyst A" described in example 1 above. The unconverted reactants as well as the products leave the reactor 100 via stream 4 and are fed to the separation system. The unconverted reactants and light hydrocarbons are recycled back in stream 2 to the reactor 100 while the separation system yields fuel gas (predominantly methane and hydrogen in stream 8 from vapor-liquid separator 200), $C_{9+}$ liquid products and benzene, toluene and xylenes (BTX).

The reactor 100 operates at about 1 atmosphere pressure and at a temperature of 675° C. while the regenerator 300, which removes the coke formed in the reactor 100, operates at around 730° C. The heat (9) required for the reaction step is provided by the hot catalyst solid mixture which is preheated during the regeneration step. In the regeneration step, catalyst containing coke flows through stream 5 to regenerator 300 and stripping gas is supplied. Regenerated catalyst flows back to the reactor 100 through stream 6 and the stripping gas exits the regenerator 300 through stream 7.

The reactor 100 achieves almost complete conversion of propane (greater than 99%) while converting about half the ethane as was the case in performance test 1 in Tables 1 and above. The average single pass mixed feed conversion is 75.49%. The liquid products are separated in a sequence of three consecutive columns to obtain the separated liquid products as shown in FIG. 1. The process yields are summarized in Table 2 below. This one stage mode of operation produces about 8.33 tph of benzene (from column 400 through stream 10), 3.25 tph toluene (from column 500 through stream 11) and 0.5 tph of mixed xylenes (from column 600 through stream 12) resulting in an overall BTX yield of 49 wt %, an overall liquid yield of 60 wt % with respect to the mixed feed. The fuel gas make (stream 8) is 9.2 tph which is about 36.7 wt % of the mixed feed.

4.2 Two-Stage Process

FIG. 2 is a schematic flow diagram for producing aromatics (benzene and higher aromatics) from a feed containing 50 wt % ethane and 50 wt % propane using a two stage reactor-regenerator system according to the present invention.

26 tonnes/hr (tph) of primarily of 50/50 ethane/propane mixed feed, including minor amounts of methane, butane, etc. (stream 1) are fed to the stage 1 aromatization reactor 100 that uses "Catalyst A" described in example 3. The first stage reactor 100 operates at about 1 atmosphere pressure and at a temperature of about 600° C. while the stage 1 regenerator 200, which removes the coke formed in the reactor 100, operates at around 730° C. The heat required for the reaction step is provided by the hot catalyst solid mixture which is preheated during the regeneration step. The reactor 100 achieves almost complete conversion of propane (greater than 98%) with minimal ethane conversion as was the case in performance test 2 in Table 3. The reactor effluent stream 3a is then mixed with the reactor effluent from the second stage reactor 300 (stream 3b), described below. The combined effluent from both the reactor stages (stream 4) is then fed to a separation system where unconverted reactants and light hydrocarbons that consist primarily of ethane and some other hydrocarbons, which may include ethylene, propane, propylene, methane, butane and some hydrogen, are used as the feed (stream 2) for the stage-2 aromatization reactor 300 which uses "catalyst B" described above.

The second stage reactor 300 operates at about 1 atmosphere pressure and a temperature of about 620° C. while the regenerator 400, which removes the coke formed in the reactor, operates at around 730° C. The heat required for the reaction step is provided by the hot catalyst solid mixture which is preheated during the regeneration step. The second stage reactor 300 converts almost half the ethane fed to it as was the case in performance test 4 in Table 3 above. The effluent from the second stage reactor 300 (stream 3b) is mixed with the effluent from the first stage reactor 100 as described above. Both stage-1 and stage-2 of the aromatization reactor system use a cyclic fixed bed design.

The average single pass conversion for the mixed feed is obtained from the cumulative conversion of ethane and propane (feeds) over both the stages and is calculated to be 75.35%. The liquid products are separated in a sequence of three consecutive columns to obtain the separated liquid products as shown in FIG. 2. The process yields are summarized in Table 4 below. This two-stage mode of operation produces about 8.4 tph of benzene (from column 600 through stream 10), 5.3 tph toluene (from column 700 through stream 11) and 1.2 tph xylenes (from column 800 through stream 12) resulting in an overall BTX yield of 60 wt % and an overall liquid yield of 57.3 wt % with respect to the mixed feed. The undesired fuel gas make (stream 8 from vapor-liquid separator 500) is about 7.6 tph which is about 29.2 wt % of the mixed feed.

4.3 Comparison of Process Configurations

Table 4 below shows the comparison of the system performance for one stage and two stage processes. The processes are compared for conditions resulting in constant overall feed conversions. The single stage process has to be operated at higher temperature as compared to each of the two stages in the two-stage process to achieve a similar feed conversion per pass. It is evident from Table 4 that the two-stage operation results in better product yields of benzene, toluene, mixed xylenes and $C_{9+}$ liquids with lower undesired fuel gas make as compared to the one stage process.

TABLE 4

| Feed (ethane/propane) Reactor (stages) | 50-50 (wt %) One stage | 50-50 (wt %) Two stages |
|---|---|---|
| Catalyst | A (stage 1) | A (stage 1) B (stage 2) |
| Average conversion per pass (%) | 75.5 | 75.35 |
| GHSV (per hr) | 1000 | 1000 (both stages) |
| Reactor Temp (° C.) | Stage-1: 675 | Stage-1: 600 Stage-2: 621 |
| Benzene yield (tonne/tonne$_{feed}$, %) | 33.3% | 32.3% |
| Toluene yield (tonne/tonne$_{feed}$, %) | 13.0% | 20.4% |
| Mixed Xylene yield (tonne/tonne$_{feed}$, %) | 2.0% | 4.6% |
| C9+ liquids yield (tonne/tonne$_{feed}$, %) | 10.33% | 6.5% |
| Total BTX yield (tonne/tonne$_{feed}$, %) | 48.3% | 57.3% |
| Total Liq yield (tonne/tonne$_{feed}$, %) | 58.7% | 63.8% |
| Total fuel-gas make (tonne/tonne$_{feed}$, %) | 36.7% | 29.2% |

Note:
All yields are expressed as tonnes of the product per tonne of the mixed feed entering the overall process, expressed as percentage.
The average conversion per pass for a two-stage process is computed as: (Total propane conversion × mol fraction of propane in the mixed feed) + (Total ethane conversion × mol fraction of ethane in the mixed feed)

Example 5

In this example the results of laboratory tests are used to represent a one-stage aromatization process vs. a two-stage process utilizing the same catalyst in each stage. The lower alkane feedstock of this example consists of 31.6 wt % ethane, 29.5 wt % propane, and 38.9 wt % n-butane, and the temperature of the second stage is higher than the temperature of the first stage.

Fresh 15-cc charges of Catalyst A (prepared as described in Example 1 above) were subjected to performance tests as described below. Performance Test 5 was conducted under conditions which might be used for a one-stage aromatization process with a mixed ethane/propane/butane feed. Performance Test 6 was conducted under conditions which might be used for the first stage of a two-stage aromatization process with a mixed ethane/propane/butane feed according to the present invention. Performance Test 3 (described in Example 1) was conducted under conditions which might be used for the second stage of a two-stage aromatization process according to the present invention.

Performance Test 5 was conducted in the same manner and under the same conditions as those used for Performance Test 1 (described in Example 1), except that the feed for Performance Test 5 consisted of 31.6 wt % ethane, 29.5 wt % propane, and 38.9 wt % n-butane. Performance Test 6 was conducted in the same manner and under the same conditions as those used for Performance Test 2 (described in Example 1), except that the feed for Performance Test 6 consisted of 31.6 wt % ethane, 29.5 wt % propane, and 38.9 wt % n-butane.

Table 5 lists the results of online gas chromatographic analyses of the total product streams from Performance Tests 5, 6, and 3. Based on composition data obtained from the gas chromatographic analysis, initial ethane, propane, n-butane and total conversions were computed according to the following formulas:

Ethane conversion, %=100×(wt % ethane in feed−wt % ethane in outlet stream)/(wt % ethane in feed)

Propane conversion, %=100×(wt % propane in feed−wt % propane in outlet stream)/(wt % propane in feed)

$n$-Butane conversion, %=100×(wt % $n$-butane in feed−wt % $n$-butane in outlet stream)/(wt % $n$-butane in feed)

Total ethane+propane+$n$-butane conversion=((wt % ethane in feed×% ethane conversion)+(wt % propane in feed×% propane conversion)+(wt % $n$-butane in feed×% $n$-butane conversion))/100

TABLE 5

| PERFORMANCE TEST | 5 | 6 | 3 |
|---|---|---|---|
| Catalyst | A | A | A |
| Catalyst volume, cc | 15 | 15 | 15 |
| Reactor wall temperature, ° C. | 675 | 600 | 621 |
| Pressure, MPa | 0.1 | 0.1 | 0.1 |
| Feed composition | | | |
| Ethane, wt % | 31.6 | 31.6 | 100 |
| Propane, wt % | 29.5 | 29.5 | -0- |
| n-Butane, wt % | 38.9 | 38.9 | -0- |
| Total feed rate, GHSV | 1000 | 1000 | 1000 |
| Total feed rate, WHSV | 2.24 | 2.24 | 1.61 |
| Ethane conversion, % | 34.02 | −30.04 | 49.28 |
| Propane conversion, % | 99.27 | 97.80 | — |
| n-Butane conversion, % | 99.80 | 99.79 | — |
| Total ethane + propane + n-butane conversion, % | 78.84 | 58.15 | 49.28 |
| Reactor outlet composition, wt % | | | |
| Hydrogen | 4.93 | 3.62 | 4.71 |
| Methane | 18.2 | 10.98 | 7.56 |
| Ethylene | 5.57 | 2.9 | 3.95 |
| Ethane | 20.86 | 41.11 | 50.72 |
| Propylene | 0.57 | 0.48 | 0.58 |
| Propane | 0.22 | 0.65 | 0.70 |
| C4 | 0.08 | 0.08 | 0.11 |

TABLE 5-continued

| PERFORMANCE TEST | 5 | 6 | 3 |
|---|---|---|---|
| C5 | 0 | 0 | -0- |
| Benzene | 28.33 | 18.89 | 16.60 |
| Toluene | 11.1 | 13.31 | 8.72 |
| C8 aromatics | 1.62 | 2.97 | 1.70 |
| C9+ aromatics | 8.52 | 5.01 | 4.65 |
| Total aromatics | 49.57 | 40.18 | 31.67 |

The negative value recorded for % ethane conversion in Table 5 for Performance Test 6 indicates that the amount of ethane made as a byproduct of propane and/or butane conversion exceeded the amount of ethane converted in this test. Nevertheless, it can be seen from Table 5 that the one stage method produced 49.57 wt % total aromatics from the given ethane/propane/n-butane feedstock, while the two stage method produced 53.20 wt % total aromatics based on a 100 wt % total feed to stage 1 followed by stage 2 which is fed with the ethane from stage 1. In a true two stage operation, it is likely that the feed to stage 2 would include all non-aromatics from the outlet of stage 1 except the fuel gas (methane and hydrogen). These non-aromatics would include not only ethane but also ethylene, propylene, propane, etc. which would likely increase the total aromatics yield to slightly more than 54 wt % based on a 100 wt % total feed to stage 1.

Example 6

Process Configuration Comparisons 6.1 One-Stage Process (Comparative)

FIG. 1 is a schematic flow diagram, which illustrates the process scheme for producing aromatics (benzene and higher aromatics) from a feed containing 31.6 wt % ethane, 29.5 wt % propane and 38.9 wt % butane using a one reactor-regenerator stage process.

25 tonnes/hr (tph) of mixed feed (stream 1), which constitutes primarily 31.6 wt % ethane, 29.5 wt % propane and 38.9 wt % butane (including minor amounts of methane, butane, etc.) is mixed with a recycle stream 2 that consists primarily of ethane and other hydrocarbons, possibly including but not limited to, ethylene, propane, propylene, methane, butane and some hydrogen. The total feed stream 3 is now introduced to the single stage aromatization reactor 100. The aromatization reactor system may be a fluidized bed, moving bed or a cyclic fixed bed design. Here the cyclic fixed bed design is used. The reactor system employs "Catalyst A" described example 5 above. The unconverted reactants as well as the products leave the reactor 100 via stream 4 and are fed to the separation system. The unconverted reactants and light hydrocarbons are recycled back in stream 2 to the reactor 100 while the separation system yields fuel gas (predominantly methane and hydrogen in stream 8 from vapor-liquid separator 200), $C_{9+}$ liquid products and benzene, toluene and xylenes (BTX).

The reactor 100 operates at about 1 atmosphere pressure and at a temperature of 675° C. while the regenerator 300, which removes the coke formed in the reactor 100, operates at around 730° C. The heat (9) required for the reaction step is provided by the hot catalyst solid mixture which is preheated during the regeneration step. In the regeneration step, catalyst containing coke flows through stream 5 to regenerator 300 and stripping gas is supplied. Regenerated catalyst flows back to the reactor 100 through stream 6 and the stripping gas exits the regenerator 300 through stream 7.

The reactor 100 achieves almost complete conversion of propane and butane (greater than 99%). The average single pass mixed feed conversion is 78.84%. The liquid products are separated in a sequence of three consecutive columns to obtain the separated liquid products as shown in FIG. 1. The process yields are summarized in Table 6 below. This one stage mode of operation produces about 9.7 tph of benzene (from column 400 through stream 10), 3.8 tph toluene (from column 500 through stream 11) and 0.6 tph of mixed xylenes (from column 600 through stream 12) resulting in an overall BTX yield of 56.2 wt %, an overall liquid yield of 67.9 wt % with respect to the mixed feed. The fuel gas make (stream 8) is 8 tph which is about 31.9 wt % of the mixed feed.

6.2 Two-Stage Process

FIG. 2 is a schematic flow diagram for producing aromatics (benzene and higher aromatics) from a feed containing 31.6 wt % ethane, 29.5 wt % propane and 38.9 wt % butane using a two stage reactor-regenerator system according to the present invention.

25 tonnes/hr (tph) of mixed feed (stream 1), which constitutes primarily 31.6 wt % ethane, 29.5 wt % propane and 38.9 wt % butane including minor amounts of methane, butane, etc. (stream 1) are fed to the stage 1 aromatization reactor 100 that uses "Catalyst A" described in example 1. The first stage reactor 100 operates at about 1 atmosphere pressure and at a temperature of about 600° C. while the stage 1 regenerator 200, which removes the coke formed in the reactor 100, operates at around 730° C. The heat required for the reaction step is provided by the hot catalyst solid mixture which is preheated during the regeneration step. The reactor 100 achieves almost complete conversion of butane and 98% conversion of propane with a negative value recorded for % ethane conversion as shown in Table 5 for Performance Test 6. This indicates that the amount of ethane made as a byproduct of propane and/or butane conversion exceeded the amount of ethane converted in this test. The reactor effluent stream 3a is then mixed with the reactor effluent from the second stage reactor 300 (stream 3b), described below. The combined effluent from both the reactor stages (stream 4) is then fed to a separation system where unconverted reactants and light hydrocarbons that consist primarily of ethane and some other hydrocarbons, which may include ethylene, propane, propylene, methane, butane and some hydrogen, are used as the feed (stream 2) for the stage-2 aromatization reactor 300 which uses "catalyst A" described above.

The second stage reactor 300 operates at about 1 atmosphere pressure and a temperature of about 620° C. while the regenerator 400, which removes the coke formed in the reactor, operates at around 730° C. The heat required for the reaction step is provided by the hot catalyst solid mixture which is preheated during the regeneration step. The second stage reactor 300 converts almost half the ethane fed to it as was the case in performance test 3 in Table 5 above. The effluent from the second stage reactor 300 (stream 3b) is mixed with the effluent from the first stage reactor 100 as described above. Both stage-1 and stage-2 of the aromatization reactor system use a cyclic fixed bed design.

The average single pass conversion for the mixed feed is obtained from the cumulative conversion of ethane, propane and butane (feeds) over both the stages and is calculated to be 74.5%. The liquid products are separated in a sequence of three consecutive columns to obtain the separated liquid products as shown in FIG. 2. The process yields are summarized in Table 6 below. This two-stage mode of operation produces about 8.9 tph of benzene (from column 600 through stream 10), 5.6 tph toluene (from column 700 through stream 11) and 1.2 tph xylenes (from column 800 through stream 12) resulting in an overall BTX yield of 62.6 wt % and an overall liquid yield of 72.4 wt % with respect to the mixed feed. The undesired fuel gas make (stream 8 from vapor-liquid separator 500) is about 6.8 tph which is about 27.3 wt % of the mixed feed.

6.3 Comparison of Process Configurations

Table 6 below shows the comparison of the system performance for one stage and two stage processes. The processes are compared for conditions resulting in constant overall feed conversions. The single stage process has to be operated at higher temperature as compared to each of the two stages in the two-stage process to achieve a similar feed conversion per pass. It is evident from Table 6 that the two-stage operation results in better product yields of benzene, toluene, mixed xylenes and C9+ liquids with lower undesired fuel gas make as compared to the one stage process.

TABLE 6

| Reactor (stages) | One stage | Two stages |
|---|---|---|
| Feed (wt %) (ethane/propane/butane) | 31.6/29.5/38.9 | 31.6/29.5/38.9 |
| Catalyst | A (stage 1) | A (stage 1) A (stage 2) |
| Average conversion per pass % | 78.84 | 74.48 |
| GHSV (per hr) | 1000 | 1000 (both stages) |
| Reactor Temp (° C.) | Stage-1: 675 | Stage-1: 600 Stage-2: 621 |
| Benzene yield (tonne/tonne$_{feed}$, %) | 38.73% | 35.7% |
| Toluene yield (tonne/tonne$_{feed}$, %) | 15.3% | 22.2% |
| Mixed Xylene yield (tonne/tonne$_{feed}$, %) | 2.2% | 4.7% |
| C9+ liquids yield (tonne/tonne$_{feed}$, %) | 11.7% | 9.8% |
| Total BTX yield (tonne/tonne$_{feed}$, %) | 56.2% | 62.6% |
| Total Liq yield (tonne/tonne$_{feed}$, %) | 67.9% | 72.4% |
| Total fuel-gas make (tonne/tonne$_{feed}$, %) | 31.9% | 27.3% |

Note:
All yields are expressed as tonnes of the product per tonne of the mixed feed entering the overall process, expressed as percentage.
The average conversion per pass for a two-stage process is computed as: (Total propane conversion × mol fraction of propane in the mixed feed) + (Total butane conversion × mol fraction of butane in the mixed feed) + (Total ethane conversion × mol fraction of ethane in the mixed feed)

Example 7

In this example the results of laboratory tests are used to represent a one-stage aromatization process vs. a two-stage process utilizing the same catalyst in each stage. The lower alkane feedstock of this example consists of 31.6 wt % ethane, 29.5 wt % propane, and 38.9 wt % n-butane, and the temperature of the second stage is the same as that of the first stage.

Fresh 15-cc charges of Catalyst A (prepared as described in Example 1 above) were subjected to performance tests as described below. Performance Test 5 (described in Example 5) was conducted under conditions which might be used for a one-stage aromatization process with a mixed ethane/propane/butane feed. Performance Test 7 was conducted under conditions which might be used for the first stage of a two-stage aromatization process with a mixed ethane/propane/butane feed according to the present invention. Performance Test 3 (described in Example 1) was conducted under conditions which might be used for the second stage of a two-stage aromatization process according to the present invention.

Performance Test 7 was conducted in the same manner and under the same conditions as those used for Performance Test 6 (described in Example 5), except that the reactor wall temperature used for Performance Test 7 was 621° C.

Table 7 lists the results of online gas chromatographic analyses of the total product streams from Performance Tests 5, 7, and 3. Based on composition data obtained from the gas chromatographic analysis, initial ethane, propane, n-butane and total conversions were computed according to the formulas given in Example 5.

TABLE 7

| PERFORMANCE TEST | 5 | 7 | 3 |
|---|---|---|---|
| Catalyst | A | A | A |
| Catalyst volume, cc | 15 | 15 | 15 |
| Reactor wall temperature, ° C. | 675 | 621 | 621 |
| Pressure, MPa | 0.1 | 0.1 | 0.1 |
| Feed composition | | | |
| Ethane, wt % | 31.6 | 31.6 | 100 |
| Propane, wt % | 29.5 | 29.5 | -0- |
| n-Butane, wt % | 38.9 | 38.9 | -0- |
| Total feed rate, GHSV | 1000 | 1000 | 1000 |
| Total feed rate, WHSV | 2.24 | 2.24 | 1.61 |
| Ethane conversion, % | 34.02 | −9.61 | 49.28 |
| Propane conversion, % | 99.27 | 98.35 | — |
| n-Butane conversion, % | 99.80 | 99.79 | — |
| Total ethane + propane + n-butane conversion, % | 78.84 | 64.77 | 49.28 |
| Reactor outlet composition, wt % | | | |
| Hydrogen | 4.93 | 4.41 | 4.71 |
| Methane | 18.2 | 11.71 | 7.56 |
| Ethylene | 5.57 | 3.61 | 3.95 |
| Ethane | 20.86 | 34.65 | 50.72 |
| Propylene | 0.57 | 0.52 | 0.58 |
| Propane | 0.22 | 0.49 | 0.70 |
| C4 | 0.08 | 0.08 | 0.11 |
| C5 | 0 | 0 | -0- |
| Benzene | 28.33 | 20 | 16.60 |
| Toluene | 11.1 | 12.21 | 8.72 |
| C8 aromatics | 1.62 | 2.45 | 1.70 |
| C9+ aromatics | 8.52 | 9.87 | 4.65 |
| Total aromatics | 49.57 | 44.53 | 31.67 |

The negative value recorded for % ethane conversion in Table 7 for Performance Test 7 indicates that the amount of ethane made as a byproduct of propane and/or butane conversion exceeded the amount of ethane converted in this test. Nevertheless, it can be seen from Table 7 that the one stage method produced 49.57 wt % total aromatics from the given ethane/propane/n-butane feedstock, while the two stage method produced 55.50 wt % total aromatics based on a 100 wt % total feed to stage 1 followed by stage 2 which is fed with the ethane from stage 1. In a true two stage operation, it is likely that the feed to stage 2 would include all non-aromatics from the outlet of stage 1 except the fuel gas (methane and hydrogen). These non-aromatics would include not only unconverted ethane but also ethylene, propylene, propane, etc. which would likely increase the total aromatics yield to slightly more than 56 wt % based on a 100 wt % total feed to stage 1.

Example 8

Process Configuration Comparisons 8.1 One-Stage Process (Comparative)

FIG. 1 is a schematic flow diagram, which illustrates the process scheme for producing aromatics (benzene and higher aromatics) from a feed containing 31.6 wt % ethane, 29.5 wt % propane and 38.9 wt % butane using a one reactor-regenerator stage process.

25 tonnes/hr (tph) of mixed feed (stream 1), which constitutes primarily 31.6 wt % ethane, 29.5 wt % propane and 38.9 wt % butane (including minor amounts of methane, butane, etc.) is mixed with a recycle stream 2 that consists primarily of ethane and other hydrocarbons, possibly including but not limited to, ethylene, propane, propylene, methane, butane and some hydrogen. The total feed stream 3 is now introduced to the single stage aromatization reactor 100. The aromatization reactor system may be a fluidized bed, moving bed or a cyclic fixed bed design. Here the cyclic fixed bed design is used. The reactor system employs "Catalyst A" described example 7 above. The unconverted reactants as well as the products leave the reactor 100 via stream 4 and are fed to the separation system. The unconverted reactants and light hydrocarbons are recycled back in stream 2 to the reactor 100 while the separation system yields fuel gas (predominantly methane and hydrogen in stream 8 from vapor-liquid separator 200), $C_{9+}$ liquid products and benzene, toluene and xylenes (BTX).

The reactor 100 operates at about 1 atmosphere pressure and at a temperature of 675° C. while the regenerator 300, which removes the coke formed in the reactor 100, operates at around 730° C. The heat (9) required for the reaction step is provided by the hot catalyst solid mixture which is preheated during the regeneration step. In the regeneration step, catalyst containing coke flows through stream 5 to regenerator 300 and stripping gas is supplied. Regenerated catalyst flows back to the reactor 100 through stream 6 and the stripping gas exits the regenerator 300 through stream 7.

The reactor 100 achieves almost complete conversion of propane and butane (greater than 99%). The average single pass mixed feed conversion is 78.84%. The liquid products are separated in a sequence of three consecutive columns to obtain the separated liquid products as shown in FIG. 1. The process yields are summarized in Table 6 below. This one stage mode of operation produces about 9.7 tph of benzene (from column 400 through stream 10), 3.8 tph toluene (from column 500 through stream 11) and 0.6 tph of mixed xylenes (from column 600 through stream 12) resulting in an overall BTX yield of 56.2 wt %, an overall liquid yield of 67.9 wt % with respect to the mixed feed. The fuel gas make (stream 8) is 8 tph which is about 31.9 wt % of the mixed feed.

8.2 Two-Stage Process

FIG. 2 is a schematic flow diagram for producing aromatics (benzene and higher aromatics) from a feed containing 31.6 wt % ethane, 29.5 wt % propane and 38.9 wt % butane using a two stage reactor-regenerator system according to the present invention.

25 tonnes/hr (tph) of mixed feed (stream 1), which constitutes primarily 31.6 wt % ethane, 29.5 wt % propane and 38.9 wt % butane including minor amounts of methane, butane, etc. (stream 1) are fed to the stage 1 aromatization reactor 100 that uses "Catalyst A" described in example 1. The first stage reactor 100 operates at about 1 atmosphere pressure and at a temperature of about 620° C. while the stage 1 regenerator 200, which removes the coke formed in the reactor 100, operates at around 730° C. The heat required for the reaction step is provided by the hot catalyst solid mixture which is preheated during the regeneration step. The reactor 100 achieves almost complete conversion of butane and propane with a negative value recorded for % ethane conversion as shown in Table 7 for Performance Test 7. This indicates that the amount of ethane made as a byproduct of propane and/or butane conversion exceeded the amount of ethane converted in this test. The reactor effluent stream 3a is then mixed with the reactor effluent from the second stage reactor 300 (stream 3b), described below. The combined effluent from both the reactor stages (stream 4) is then fed to a separation system where unconverted reactants and light hydrocarbons that consist primarily of ethane and some other hydrocarbons, which may include ethylene, propane, propylene, methane, butane and some hydrogen, are used as the feed (stream 2) for the stage-2 aromatization reactor 300 which uses "catalyst A" described above.

The second stage reactor 300 operates at about 1 atmosphere pressure and operates at the same temperature as that of the first stage (620° C.), while the regenerator 400, which removes the coke formed in the reactor, operates at around 730° C. The heat required for the reaction step is provided by the hot catalyst solid mixture which is preheated during the regeneration step. The second stage reactor 300 converts almost half the ethane fed to it as was the case in performance test 3 in Table 7 above. The effluent from the second stage reactor 300 (stream 3*b*) is mixed with the effluent from the first stage reactor 100 as described above. Both stage-1 and stage-2 of the aromatization reactor system use a cyclic fixed bed design.

The average single pass conversion for the mixed feed is obtained from the cumulative conversion of ethane, propane and butane (feeds) over both the stages and is calculated to be 80.9%. The liquid products are separated in a sequence of three consecutive columns to obtain the separated liquid products as shown in FIG. 2. The process yields are summarized in Table 8 below. This two-stage mode of operation produces about 8.6 tph of benzene (from column 600 through stream 10), 5 tph toluene (from column 700 through stream 11) and 1 tph xylenes (from column 800 through stream 12) resulting in an overall BTX yield of 58.5 wt % and an overall liquid yield of 72.5 wt % with respect to the mixed feed. The undesired fuel gas make (stream 8 from vapor-liquid separator 500) is about 6.8 tph which is about 27.2 wt % of the mixed feed.

8.3 Comparison of Process Configurations

Table 6 below shows the comparison of the system performance for one stage and two stage processes. The processes are compared for conditions resulting in constant overall feed conversions. The single stage process has to be operated at higher temperature as compared to each of the two stages in the two-stage process to achieve a similar feed conversion per pass. It is evident from Table 8 that the two-stage operation results in better product yields of benzene, toluene, mixed xylenes and $C_{9+}$ liquids with lower undesired fuel gas make as compared to the one stage process.

TABLE 8

| Reactor (stages) | One stage | Two stages |
|---|---|---|
| Feed (wt %) (ethane/propane/butane) | 31.6/29.5/38.9 | 31.6/29.5/38.9 |
| Catalyst | A (stage 1) | A (stage 1) |
|  |  | A (stage 2) |
| Average conversion per pass % | 78.84 | 80.94 |
| GHSV (per hr) | 1000 | 1000 (both stages) |
| Reactor Temp (° C.) | Stage-1: 675 | Stage-1: 621 |
|  |  | Stage-2: 621 |
| Benzene yield (tonne/tonne$_{feed}$, %) | 38.73% | 34.6% |
| Toluene yield (tonne/tonne$_{feed}$, %) | 15.3% | 20% |
| Mixed Xylene yield (tonne/tonne$_{feed}$, %) | 2.2% | 3.96% |
| C9+ liquids yield (tonne/tonne$_{feed}$, %) | 11.7% | 14.0% |
| Total BTX yield (tonne/tonne$_{feed}$, %) | 56.2% | 58.5% |

TABLE 8-continued

| Reactor (stages) | One stage | Two stages |
|---|---|---|
| Total Liq yield (tonne/tonne$_{feed}$, %) | 67.9% | 72.5% |
| Total fuel-gas make (tonne/tonne$_{feed}$, %) | 31.9% | 27.2% |

Note:
All yields are expressed as tonnes of the product per tonne of the mixed feed entering the overall process, expressed as percentage.
The average conversion per pass for a two-stage process is computed as: (Total propane conversion × mol fraction of propane in the mixed feed) + (Total butane conversion × mol fraction of butane in the mixed feed) + (Total ethane conversion × mol fraction of ethane in the mixed feed)

What is claimed is:

1. A process for the conversion of mixed lower alkanes into aromatics which comprises first reacting a mixed lower alkane feed comprising at least propane and ethane in the presence of an aromatization catalyst under first stage reaction conditions at a first temperature which maximize the conversion of propane into first stage aromatic reaction products, separating ethane from the first aromatic reaction products, reacting ethane in the presence of an aromatization catalyst under second stage reaction conditions at a second temperature which maximize the conversion of ethane into second stage aromatic reaction products, and optionally separating ethane from the second stage aromatic reaction products; wherein the second temperature is higher than the first temperature.

2. The process of claim 1 wherein the aromatization reaction is carried out at a temperature of from 400 to 700° C.

3. The process of claim 1 wherein the first stage reaction conditions comprise a temperature of from 400 to 650° C.

4. The process of claim 1 wherein the second stage reaction conditions comprise a temperature of from 450 to 680° C.

5. The process of claim 1 wherein the first stage reaction products are produced in at least two reactors aligned in parallel.

6. The process of claim 1 wherein the second stage reaction products are produced in at least two reactors aligned in parallel.

7. The process of claim 1 wherein other non-aromatic hydrocarbons are produced in the first stage and are reacted in the second stage along with the ethane to produce additional second stage aromatic reaction products.

8. The process of claim 1 wherein fuel gas is also produced in either or both of the first and second stages and is separated from the aromatic reaction products and ethane.

9. A process for the conversion of mixed lower alkanes into aromatics which comprises first reacting a mixed lower alkane feed comprising at least propane and ethane in the presence of an aromatization catalyst under first stage reaction conditions which maximize the conversion of propane and any other higher hydrocarbons present in the feed into first stage aromatic reaction products, separating the first aromatic reaction products from ethane and any other non-aromatic hydrocarbons produced in the first stage, reacting ethane and at least a portion of the any other non-aromatic hydrocarbons produced in the first stage in the presence of an aromatization catalyst under second stage reaction conditions which maximize the conversion of ethane and the any other non-aromatic hydrocarbons into second stage aromatic reaction products, and optionally separating the second stage aromatic reaction products from ethane and other non-aromatic hydrocarbons.

10. The process of claim 9 wherein the aromatization reaction is carried out at a temperature of from 400 to 700° C.

11. The process of claim 1 wherein the first stage reaction conditions comprise a temperature of from 400 to 650° C.

12. The process of claim 1 wherein the second stage reaction conditions comprise a temperature of from 450 to 680° C.

13. The process of claim 1 wherein the first stage reaction products are produced in at least two reactors aligned in parallel.

14. The process of claim 1 wherein the second stage reaction products are produced in at least two reactors aligned in parallel.

15. The process of claim 1 wherein fuel gas is also produced in either or both of the first and second stages and is separated from the aromatic reaction products and ethane.

* * * * *